US00PP32270P3

(12) United States Plant Patent
Cain

(10) Patent No.: US PP32,270 P3
(45) Date of Patent: Oct. 6, 2020

(54) GRAPEVINE PLANT NAMED 'IFG THIRTY-NINE'

(50) Latin Name: ***Vitis interspecific* hybrid**
Varietal Denomination: IFG Thirty-nine

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 16/350,702

(22) Filed: Dec. 26, 2018

(65) Prior Publication Data

US 2020/0214188 P1 Jul. 2, 2020

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207, 205
CPC ..... A01H 5/0812; A01H 5/08; A01H 5/02; A01H 5/0806; A01H 6/88; A01H 5/12; A01H 6/78
See application file for complete search history.

(56) References Cited

U.S. PATENT DOCUMENTS

PP29,651 P2 9/2018 Cain

*Primary Examiner* — June Hwu

(57) ABSTRACT

This invention is a new and distinct grapevine variety denominated 'IFG Thirty-nine'. The new grapevine is characterized by producing medium size narrow finger shaped yellow-green berries having medium firm texture with a muscat flavor and which ripen in mid-season. Berries are borne on medium size clusters which are naturally loose and do not require gibberellin applications to thin clusters.

1 Drawing Sheet

Latin name of the genus and species claimed: *Vitis interspecific* hybrid.

Variety denomination: 'IFG Thirty-nine'.

BACKGROUND OF THE INVENTION

The new and distinct Grapevine plant described and claimed herein originated from a hand pollinated cross of 'IFG 04150-020-228' (unpatented), a *Vitis vinifera* selection from the IFG breeding program, and 'IFG Twenty-nine' (U.S. Plant Pat. No. 29,651) hybridized in May 2010. The present variety of grapevine was selected as a single plant in August 2013 and was first asexually propagated by hardwood cuttings in December 2013 near Delano, Kern County, Calif. These resulting cuttings produced second generation plants that were planted during April 2014 near Delano, Kern County, Calif. and were observed for 4 years and found to reproduce true-to-type.

BRIEF SUMMARY OF THE INVENTION

The new grapevine 'IFG Thirty-nine' is characterized by producing medium size narrow finger shaped yellow-green berries having medium firm texture with a muscat flavor and which ripen in mid-season. Berries are borne on medium size clusters which are naturally loose and do not require gibberellin applications to thin clusters. Berry size can be increased by applying gibberellic acid. Berries store well and can be maintained in good condition for up to 8 weeks in cold storage. Clusters may occasionally exhibit some pink berries when exposed to high light intensity and stress. To the inventor's knowledge, the known variety to which the new grapevine variety is most similar is the Centennial Seedless variety (Table grape; U.S. Plant Pat. No. 4,784). 'IFG Thirty-nine' differs from 'Centennial Seedless' by having smaller berry size, firmer berries, with a narrower, more tapered finger shaped, lighter yellow-green skin color, strong muscat flavor and better storage ability.

'IFG Thirty-nine' differs from its maternal parent the 'IFG 04150-020-228' (unpatented seedling selection in the IFG breeding program) by having a narrower cylindrical to fingered shape berry shape and having a smaller berry size and more tapered tip. 'IFG Thirty-nine' is like its paternal parent, 'IFG Twenty-nine' by producing very elongated narrow pointed yellow-green berries. 'IFG Thirty-nine' differs from its paternal parent, 'IFG Twenty-nine' by having large soft seed traces and possessing a strong muscat flavor as opposed to the slightly larger diameter neutral flavored grapes of 'IFG Twenty-nine'. 'IFG Thirty-nine' exhibits better storage ability and less skin browning compared to 'IFG Twenty-nine'.

BRIEF DESCRIPTION OF THE DRAWING

The accompanying photographic drawing in FIG. 1 illustrates in full color 'IFG Thirty-nine'. The photograph was taken outdoors with indirect lighting. The colors are as nearly true as is reasonably possible in a color representation of this type.

The left side of the drawing has a mature leaf.

A mature natural fruit cluster is represented in the center of the drawing along with a typical berry in cross section.

A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 4-year-old plants of 'IFG Thirty-nine' plants grown in the vicinity of Delano, Kern County, Calif. during 2017 and 2018 and is believed to apply to plants of the variety grown under similar conditions of soil and climate elsewhere:

VINE

General:

*Vigor*.—Vigorous.
*Density of foliage*.—Dense.
*Productivity*.—Very productive, producing about 31.4 to 47.0 kg of fruit per vine.
*Root stock*.—Own root.
*Training method*.—Typically spur pruned leaving 2 bud spurs.
*Plant hardiness zone*.—Fully hardy in USDA zone 9A (2012). Not tested in other zones.

Trunk:

*Trunk diameter of* 4-*year-old vines at* 30 *cm above the soil line*.—Approximately 5.9 cm.
*Shape*.—Medium.
*Straps*.—Very long, continuous.
*Surface texture*.—Medium rough texture.
*Inner bark color*.—The following colors were observed: Greyed-orange: 175A and 166A.
*Outer bark color*.—The following colors were observed: Brown: N200B and Greyed-orange: 177A.

SHOOTS

Young shoot:

*Form of tip*.—Wide open.
*Distribution of anthocyanin coloration of tip*.—Absent.
*Intensity of anthocyanin coloration of tip*.—Absent.
*Density of prostrate hairs on tip*.—Dense.
*Density of erect hairs on tip*.—Very sparse.
*Color*.—Yellow-green: 144B.

Woody shoot (mature canes):

*Internode length*.—Long: About 14.3 cm.
*Width at node*.—About 1.4 cm.
*Cross section*.—Circular.
*Surface*.—Striate.
*Main color*.—The following colors were observed: Greyed-orange: 165B and 165C and 176A.
*Density of erect hairs on nodes*.—None.
*Density of erect hairs on internodes*.—None or very sparse.
*Axillary shoot length at full bloom*.—Weak to medium.

Flowering shoot:

*Vigor during flowering*.—Medium.
*Attitude during flowering on shoots not tied*.—Semi-drooping.
*Color*.—Dorsal side of internodes — Yellow-green: 144A, with Red-purple stripes: 59A.
*Color*.—Ventral side of internodes — Yellow-green: 144A.
*Color*.—Dorsal side of nodes — Yellow-green: 144A, with Red-purple stripes: 59A.
*Color*.—Ventral side of nodes — Yellow-green: 144A.
*Density of prostrate hairs on nodes*.—Very sparse.
*Density of erect hairs on nodes*.—None.
*Density of prostrate hairs on internodes*.—Sparse.
*Density of erect hairs on internodes*.—None.
*Anthocyanin coloration of buds*.—Absent.

Tendrils:

*Distribution on the shoot* (*at full flowering*).—Discontinuous.
*Length of tendril*.—Long: About 22.9 cm.
*Thickness of tendril* 2 *cm from base*.—About 1.8 mm.
*Color*.—Yellow-green: N144A.
*Form*.—Bifurcated and trifurcated.
*Number of consecutive tendrils*.—2.

LEAVES

Young leaves:

*Color of upper surface of first four distal unfolded leaves*.—Yellow-green: 144A.
*Color of lower surface of young leaves*.—Yellow-green: 146B.
*Average intensity of anthocyanin coloration of six distal leaves prior to flowering*.—Absent.
*Density of prostrate hairs between veins* (*lower surface*).—Medium to dense.
*Density of prostrate hairs on veins* (*lower surface*).—Medium.
*Density of erect hairs between veins* (*lower surface*).—Absent.
*Density of erect hairs on veins* (*lower surface*).—Very sparse.

Mature leaves (opposite first cluster):

*Average length*.—About 16.8 cm.
*Average width*.—About 20.8 cm.
*Mature leaf size*.—Large.
*Shape of blade*.—Wedge-shaped.
*Number of lobes*.—5.
*Blade venation*.—Palmate.
*Anthocyanin coloration of main veins on upper side of blade*.—Absent.
*Mature leaf profile*.—Undulate.
*Blistering surface of blade upper surface*.—Weak.
*Leaf blade tip*.—In the horizontal plane of the leaf. Mid-vein does not appear to curve downward.
*Leaf apex*.—Acute.
*Leaf margin*.—Serrate.
*Undulation of margin*.—Slight.
*Undulation of blade between main and lateral veins*.—Slight undulation over entire area.
*Shape of teeth*.—Mixture of both sides straight and both sides convex.
*Length of teeth*.—Long.
*Ratio length/width of teeth*.—Medium.
*Shape of upper lateral sinuses*.—Lobes slightly overlapping.
*Depth of upper lateral sinuses*.—Deep.

*General shape petiole sinus*.—Slightly open with a few leaves being half open.
*Shape of base of upper leaf sinuses*.—V-shaped.
*Tooth at petiole sinus*.—Absent.
*Density of prostrate hairs between veins on lower surface of blade*.—Medium to dense.
*Density of erect hairs between veins on lower surface of blade*.—Very sparse.
*Density of prostrate hairs on main veins on lower surface of blade*.—Dense.
*Density of erect hairs on main veins on lower surface of blade*.—Sparse.
*Density of prostrate hairs on main veins on upper surface of blade*.—Sparse.
*Density of erect hairs on main veins on upper surface of blade*.—None or very sparse.
*Autumn coloration of leaves*.—The following colors were observed: Greyed-yellow: 162A and 162B.

Upper surface:
*Color*.—Green: 137A.
*Anthocyanin coloration of main veins* (*lower surface*).—Absent.
*Color of main veins*.—Yellow-green: 145B.
*Surface appearance*.—Dull.
*Blistering surface of blade*.—Medium.

Lower surface:
*Color*.—Yellow-green: 146A.
*Anthocyanin coloration of main veins* (*lower surface*).—Absent.
*Color of main veins*.—Yellow-green: 150D.
*Glossiness*.—Weak.
*Surface texture*.—Smooth.
*Surface appearance*.—Dull.

Petiole:
*Length*.—About 16.0 cm.
*Diameter of petiole 2 cm from blade*.—About 3.3 mm.
*Petiole color*.—The following colors were observed: Yellow-green: 145A and Greyed-purple: 187C.
*Length of petiole compared to middle vein*.—Slightly shorter to equal.
*Density of prostrate hairs on petiole*.—None or very sparse.
*Density of erect hairs on petiole*.—None.

Buds:
*Bud fruitfulness*.—Basal: mostly fruitful.
*Position of first fruitful shoot on previous season cane*.—$1^{st}$ to $2^{nd}$ node.
*Dormant bud length*.—About 5.6 mm.
*Dormant bud width in the proximal/distal plane*.—About 4.6 mm.
*Dormant bud color*.—The following colors were observed: Greyed-orange: 175A and 175B.
*Time of bud burst*.—Late season: About Mar. 23, 2018.

FLOWERS

General:
*Flower sex*.—Hermaphrodite.
*Length of single flower, unopened*.—About 4.3 mm.
*Width of single flower*.—Unopened: About 2.2 mm. Opened: About 8.6 mm.
*Stamen length*.—About 4.5 mm.
*Stamen count*.—5.
*Pollen color*.—Yellow: 10B.
*Pistil length*.—About 2.9 mm.
*Pistil color*.—Yellow-green: 144A.
*Length of first inflorescence*.—Medium.
*Position of first flowering and fruiting node*.—$2^{nd}$ to $4^{th}$ node (current season growth).
*Number of inflorescence per flowering shoot*.—Up to 1: About 1.
*Time of bloom*.—Mid-season as compared with similar varieties in the growing area of Delano, Calif.
*Date of full bloom*.—About May 9, 2018.

FRUIT

General:
*Ripening period*.—Mid-season: Approximately Aug. 11, 2018.
*Use*.—Fresh market.
*Keeping quality*.—Excellent, remains commercially acceptable when stored up to 8 weeks at 0° C. and high relative humidity.
*Resistance/susceptibility to typical pests and disease of Vitis vinifera species*.—Not observed to date.
*Refractometer test*.—Soluble solids: About 18.8 Brix.
*Brix/acid*.—About 39.2.
*Titratable acidity*.—About 0.48.
*Juice ph*.—About 3.8.
*Juice color*.—Yellow-green: 145C.

Cluster:
*Mature cluster length* (*peduncle excluded*).—About 25.4 cm.
*Mature cluster width*.—About 17.1 cm.
*Mature cluster weight*.—About 1045 g.
*Bunch density*.—Loose.
*Number of berries*.—About 260.
*Form*.—Conical.

Peduncle:
*Lignification of peduncle*.—Weak.
*Diameter of peduncle*.—Approximately 4.7 mm.
*Length of peduncle*.—Short: Approximately 2.7 cm.
*Color of peduncle*.—Yellow-green: 144A.

Berry:
*Uniformity of size*.—Uniform.
*Single berry weight*.—About 5.2 g natural; to about 6.4 g when treated with gibberellic acid.
*Shape*.—Finger-shaped.
*Seeds*.—Contains small rudimentary seed traces.
*Cross section*.—Circular.
*Berry dimensions*.—Longitudinal axis: About 4.2 cm; horizontal axis: About 1.4 cm.
*Pedicel length*.—About 9.6 mm.
*Pedicel width*.—About 1.1 mm.
*Pedicel color*.—Yellow-green: 144A.
*Berry firmness*.—Firm.
*Particular flavor*.—Muscat.
*Bloom* (*cuticular wax*).—Medium.
*Berry separation from pedicel*.—Moderate.
*Skin color* (*without bloom*).—The following colors were observed: Yellow-green: 145A and 145B and 145C.
*Flesh color*.—Green-white: 157A.
*Anthocyanin coloration of flesh*.—Absent.

Skin:
*Thickness*.—Medium.
*Skin toughness*.—Not notable when chewing.
*Reticulation*.—Absent.
*Tenacity*.—Tenacious to flesh.

What is claimed:

1. A new and distinct variety of grapevine plant as herein illustrated and described.

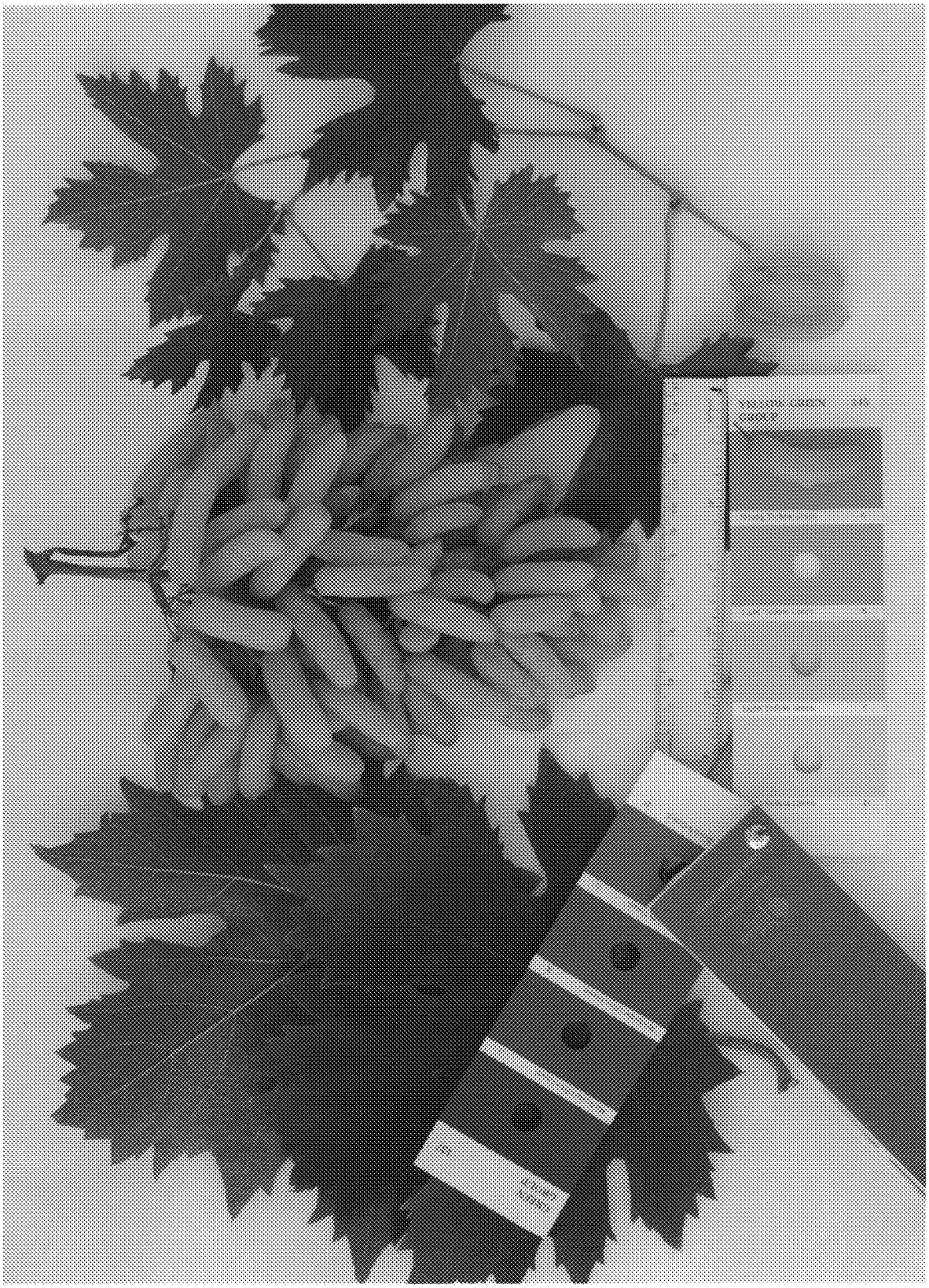

* * * * *